United States Patent [19]

Su et al.

[11] Patent Number: 4,493,783

[45] Date of Patent: Jan. 15, 1985

[54] CLEANING AGENT FOR OPTICAL SURFACES

[75] Inventors: Kai C. Su; Leslie F. Stebbins, both of Roswell, Ga.; Rajkumar P. Bhatia, Arlington, Tex.

[73] Assignee: Alcon Laboratories, Inc., Fort Worth, Tex.

[21] Appl. No.: 470,181

[22] Filed: Feb. 28, 1983

Related U.S. Application Data

[63] Continuation-in-part of Ser. No. 255,861, Apr. 20, 1981, abandoned.

[51] Int. Cl.[3] .......................... C11D 7/26; A61K 7/00

[52] U.S. Cl. .................................. 252/174.23; 134/7; 134/42; 252/106; 252/163; 252/165; 252/173; 252/174.15; 252/174.17; 252/174.21; 252/542; 252/544; 252/DIG. 2; 252/DIG. 14

[58] Field of Search .................. 252/89.1, 173, 174.23, 252/174.15, 174.17, 163, 164, 165, DIG. 10, DIG. 2, 542, 544; 424/57, 78, 81; 134/7; 51/298; 523/223; 525/7, 7.1

[56] References Cited

U.S. PATENT DOCUMENTS

| | | | |
|---|---|---|---|
| 2,780,568 | 2/1957 | Clark | 134/7 |
| 2,802,228 | 8/1957 | Federighi et al. | 15/95 |
| 3,012,262 | 12/1961 | Mori | 15/3 |
| 3,116,578 | 12/1960 | Bottler | 51/316 |
| 3,142,590 | 7/1964 | Hergonson | 134/7 |
| 3,205,620 | 9/1965 | Woodworth et al. | 51/8 |
| 3,272,650 | 9/1966 | MacVittie | 134/7 |
| 3,272,652 | 9/1966 | Wood | 134/34 |
| 3,425,870 | 2/1969 | March | 134/6 |
| 3,645,904 | 2/1972 | Beach | 252/174.23 |
| 3,734,686 | 5/1973 | Douglas | 8/137 |
| 3,790,488 | 2/1974 | Iino | 252/174.23 |
| 3,819,525 | 6/1974 | Hattenbrun | 252/132 |
| 3,884,826 | 5/1975 | Phares, Jr. et al. | 252/106 |
| 3,910,296 | 10/1975 | Karageozian et al. | 134/2 |
| 3,954,644 | 5/1976 | Krezanoski et al. | 252/106 |
| 4,028,261 | 6/1977 | Petersen et al. | 252/89 |
| 4,029,817 | 6/1977 | Blanco et al. | 424/329 |
| 4,127,423 | 11/1978 | Rankin | 134/30 |
| 4,152,283 | 5/1979 | Cordrey et al. | 252/99 |
| 4,167,488 | 9/1979 | Murtaugh | 252/160 |
| 4,242,842 | 1/1981 | Yancey | 51/298 |
| 4,246,257 | 1/1981 | Elliott et al. | 424/78 |
| 4,260,396 | 4/1981 | Glemza | 51/298 |
| 4,394,179 | 7/1983 | Ellis et al. | 134/7 |
| 4,413,070 | 11/1983 | Rembaum | 523/223 |

FOREIGN PATENT DOCUMENTS

| | | |
|---|---|---|
| 2555504 | 7/1977 | Fed. Rep. of Germany . |
| 1255039 | 1/1961 | France . |
| 2101735 | 3/1972 | France . |
| 2339180 | 8/1977 | France . |
| 2459993 | 1/1981 | France . |
| 59105 | 8/1973 | Japan . |
| 1458816 | 12/1976 | United Kingdom . |

*Primary Examiner*—Prince E. Willis

*Attorney, Agent, or Firm*—Fitch, Even, Tabin & Flannery

[57] ABSTRACT

Soft and hard contact lenses are freed from deposits by rubbing them with a particulate organic polymer with a carrier, the polymer having a particular size in the range from about one micron to about 600 microns and a Rockwell hardness in the range of from about R120 to about M68, or a shore hardness in the range from about A15 to about D100.

19 Claims, No Drawings

CLEANING AGENT FOR OPTICAL SURFACES

This application is a continuation-in-part of application Ser. No. 255,861 filed Apr. 20, 1981, now abandoned.

This invention relates to a cleansing composition for optical surfaces such as contact lenses and similar optic apparatuses.

Cleansing compositions containing various abrasive materials have been used in the past. The abradant material is added to the composition to increase the effectiveness of the composition in removing undesired matter from the surface being cleaned. Heretofore the abradants, even when in fine particle form, were harsh and had a tendency to scratch optical surfaces.

Efficient cleaning of optical surfaces without damaging them when such surfaces become encrusted with foreign matter sometimes presents difficult problems. Contact lenses that have developed heavy proteinaceous or other encrustations present particularly difficult cleaning problems. Encrustations that form on contact lenses may be proteinaceous in nature or may be lipids or other materials foreign to the eye such as lady's mascara which usually is a soap or wax in gelatin. Success in wearing and properly using contact lenses is a function of maintaining them in a clean condition without the buildup of foreign matter, particularly encrustations which physically or chemically attach to the lens surface. Buildup of such material is gradual, but will ultimately render the lens opaque. Even before the lens becomes opaque, however, the presence of encrustations on the lens causes the wearer of the lens increased discomfort and irritation.

Hard contact lenses usually are made of polymethylmethacrylate (PMMA). PMMA has excellent clarity, but has poor scratch resistance. The hardness of PMMA may be evaluated in a variety of ways, but on a relative scale of hardness, which are derived by crude scratch tests, PMMA lenses have the following relative hardness (according to "Corneal and scleral contact lenses", Proceedings of the International Congress, Louis J. Girard, M.D., Editor and Forsythe; and, Smithsonian physical tables, ed. 9, Washington, D.C. 1959, Smithsonian Press):

| | Relative Hardness |
|---|---|
| Diamond | 10 |
| Glass | 4.5–6.5 |
| PMMA | 3 |

The Rockwell hardness of PMMA ranges from about M85 to about M105. As a result, PMMA is more vulnerable to scratching than even a poor grade of glass.

Hard contact lenses may be buffed to remove encrustations, but such a process requires skill and is not easily done by the user at home without the considerable danger of scratching the lens. Hence, the user of hard contact lenses is presented with difficult cleaning problems as to encrustations and their removal at home. Further, the surface of a soft contact lens is particularly prone to develop encrustations and presents particularly difficult cleaning problems since soft contact lenses cannot be cleaned except by professionals and then only with limited success.

Many different solutions have been formulated for cleaning contact lenses. The compositions, however, are primarily directed to disinfecting lenses and generally do not remove encrustations. Those compositions that have been formulated for the purpose of removing encrustations have met with limited success.

Soft contact lenses may be divided into two broad categories, namely, hydrophilic and hydrophobic lenses. Hydrophobic contact lenses are usually based on elastic and flexible silicone rubber (polysiloxane), and are generally made from cross-linked dimethyl polysiloxane.

Hydrophilic soft contact lenses are a hydrated gel, and their ability to absorb water results in swelling to a transparent soft mass of good mechanical strength which is very comfortable to the wearer. Hydrated gel lenses can contain: hydroxyethylmethacrylate (HEMA) or its analogs, ethylene-glycol dimethacrylate (EGMA) or its analogs, polymethylmethacrylate (PMMA) or its analogs, polyvinylpyrrolidone (PVP) or its analogs, monomers, traces of catalysts and water. Hydrophilic groups of these plastic lenses attract and hold large amounts of water in the gel. These virtues, however, lead to difficulties in cleaning and sterilizing the lenses.

Hydrophilic soft lenses may be disinfected by chemical treatment or by boiling. As indicated, neither procedure is entirely successful in removing encrustations. Some chemicals are ineffective in removing proteins, others in removing lipids. Boiling may even denature proteinaceous material on the lenses thereby attaching encrustations all the more firmly to the lenses. U.S. Pat. No. 3,910,296 to Karageozian et al., discusses a method for removing proteinaceous deposits from contact lenses with the use of a protease, however, lenses may become encrusted and contaminated with other deleterious materials such as lipids which protease enzyme will not remove.

The highly hydrophobic nature of the contact lenses based upon silicone rubber interferes with their uniform and effective cleaning. U.S. Pat. No. 4,127,423 to Rankin discusses a method of cleansing encrusted soft contact lenses including silicone lenses, with aqueous solutions of sodium silicates. Deionized water is required and boiling is required when the lenses are heavily encrusted.

U.S. Pat. No. 3,954,644 to Krezanoski et al. discusses a contact lens cleaning, storing and wetting solution. The solution discussed contains a poly(oxyethylene)-poly(oxypropylene) block copolymer which is the primary wetting and cleaning agent of the composition. Elimination of encrustations from the surface of the lens is not discussed.

A need exists, therefore, for a cleansing composition which can remove foreign deposits and encrustations from both hard and soft surfaces without adversely affecting the surfaces thereof. More particularly, a need exists for a cleansing composition which can clean and remove foreign deposits from both soft and hard contact lenses, and particularly from soft contact lenses.

In accordance with the present invention, the use of particulate organic polymers or polysiloxane having particle sizes between one and six hundred microns suspended in a suitable carrier unexpectedly provides a composition which can clean, without damage, soft or delicate surfaces including hard or soft contact lenses.

To provide a cleansing composition, the particulate polymer is mixed with a carrier which is compatible with ocular tissue. The carrier usually contains or includes a thickening agent such as carboxy vinyl polymers of high molecular weight sold under the name of Carbopol (a registered trademark of B. F. Goodrich Chemical Co.), cellulose or polyethylene glycol with a molecular weight distribution of 400 to 4000 hydroxyethyl cellulose, methoxy cellulose, low molecular weight HEMA, polyvinyl alcohol and PVP to form a suspension. The carrier can be any ocular compatible composition in which the polymeric particulates remain in suspension. Most generally the carrier is water to which various optional ingredients may be added. The end product may be a fluid or may be a thixotropic ointment or gel. A surfactant such as Pluronic, (a registered trademark of Wyanclotte Chemicals Co.), Tween, (a registered trademark of Atlas Powder Company) or tyloxapol may be optionally be added to the cleaning composition to increase its effectiveness. Thimerosal (a product of Eli Lilly & Co.), sorbic acid, or ethylenediamintetraacetic acid (EDTA), as preservatives or bactericides, sodium chloride, and purified water may be optionally employed as is known in the art to provide a sterile, buffered, isotonic cleansing composition for contact lenses. Preferably, the surfactant is non-ionic, but cationic and anionic surfactants may be used.

According to the present invention, a suspension is prepared containing a particulate organic polymer or polysiloxane of a particle size of one to six hundred microns, the particulate polymer forming 1 to 25 percent by weight of the suspension, a surfactant, and a sufficient amount of a thickener to give the suspension a viscosity of between about 150 and about 1500 cps. The thickener keeps the polymeric particles in suspension and any viscosity suspension that will accomplish this result may be used. The polymeric particles are preferably substantially spherical, have a particle size range preferably between about twenty and about one hundred microns, and preferably form 5 to 20 percent by weight of the suspension. A particle size above and below the twenty to one hundred micron range will function; however, the smaller sized particles will take longer to complete their cleaning function and larger particles will feel gritty to the user.

Generally, as to hard contact lenses (those which are PMMA lenses having a Rockwell hardness in the range of from about M85 to about M105), the optical or lens surface being cleaned should be harder than the particulate polymer being used to clean the optical surface. If the particulate polymer being used in accordance with the invention is substantially spherical, i.e., without an irregular surface, however, the particulate polymer may be harder than the optical surface and will clean it without damage. Polymers that are completely spherical, however, are less preferred because their surface is so completely regular that their cleaning action is less efficient. Substantially spherical polymeric particulate powders are made through a precipitation process such that they have a surface sufficiently regular in shape that they will not scratch a hard or soft contact lens without regard to hardness. It is the precipitation process which gives the particles a surface which is regular and without edges. This is as compared to polymeric powders which are made by mechanical grinding which creates edges on the polymeric particles which potentially scratch optical surfaces. Polymers which may be substantially spherical or made by a precipitation process include but are not limited to polyethylene, cellulose acetate butyrate, polycarbonate, polyvinyl chloride and Nylon 11.

Nylon 6 or poly(caprolactam) which has the formula $$-\!\left(CH_2CH_2CH_2CH_2CH_2\overset{\overset{O}{\|}}{C}-NH\right)\!-,$$

Nylon 11 or poly(11-undecamide), which has the formula $$-\!\left(CH_2(CH_2)_8-CH_2\overset{\overset{O}{\|}}{C}N\right)\!-,$$

Nylon 12 or poly(lauryl lactam), which has the formula $$-\!\left(CH_2(CH_2)_9CH_2\overset{\overset{O}{\|}}{C}-NH\right)\!-$$

or mixtures thereof with Rockwell hardnesses of R80-83, R-108, and R-106, respectively, and particle size ranges of 1 to 80 microns, 1 to 80 microns, and 20 to 45 microns, respectively, all may be used as polymeric particulates. Nylon 11 is a preferred polymer. Polyethylene glycol is a preferred thickener in amounts of between about 20 and about 80 percent by weight of the suspension, preferably between about 25 and about 50 percent by weight. The following polymers with their hardnesses as indicated in TABLE 1 will serve as a suitable particulate polymers in the invention.

TABLE I

SUITABLE PARTICULATE POLYMERS*

| POLYMER | SHORE HARDNESS | ROCKWELL HARDNESS | MOLECULAR WEIGHT | TRUE DENSITY (gm/ml) |
|---|---|---|---|---|
| acrylonitrile-butadiene-styrene | | R75-115 | — | 1.04 |
| acetal or 1,1 diethoxyethane | | M94 | — | — |
| polymethylmethacrylate (PMMA) | | M85-105 | 12,000[2] | 1.20[1] |
| methylmethacrylate/styrene copolymer | | M75 | — | — |
| ethyl cellulose | | R50-115 | — | 1.14[1] |
| cellulose acetate butyrate | | R30-115 | — | 1.25[1] |
| cellulose acetate | | R85-120 | — | 1.30[1] |
| polytetrafluoroethylene | D50-55 | | — | 2.00[1] |
| polychlorotrifluorethylene | | R75-95 | — | — |
| modified polyethylene-tetrafluoroethylene (PE—TFE) | | R50 | — | — |
| ionomer[5] (copolymers of ethylene) and methacrylic acid or poly- | D50-65 | | — | — |

TABLE I-continued

SUITABLE PARTICULATE POLYMERS*

| POLYMER | SHORE HARDNESS | ROCKWELL HARDNESS | MOLECULAR WEIGHT | TRUE DENSITY (gm/ml) |
|---|---|---|---|---|
| ethylene modified with methacrylic acid. | | | | |
| fluoro ethylene polymer (FEP) fluoroplastic | D50-65 | | — | — |
| Nylon 6 or poly (caprolactam) | | R80-83 | — | 1.08[1] |
| Nylon 6/6 or poly (hexamethylene) adipamide | | R114-120 | — | 1.14[1] |
| Nylon 11 or poly (11-undecamide) | | R108 | — | 1.04[1] |
| Nylon 12 or poly (lauryl lactam) | | R106 | — | 1.01[1] |
| polybutadiene | | R40 | 200,000 to 300,000[3] | 1.01[1] |
| polyarylether | | R117 | — | — |
| polycarbonate | | M70 | 20,000 to 25,000[3] | 1.20[1] |
| PBT polyester or poly | | M68-78 | — | — |
| (butylene terephthalate) | | M68-78 | — | — |
| polyethylene | | R50 | 1,500-100,00[4] | 0.91 to 0.94[4] |
| polypropylene | | R80 | — | 0.90 to 0.92[4] |
| polysulfone | | R88 | 30,000[2] | 1.24[1] |
| silicone | A15-65 | | — | 0.98[1] |

*ASTM test method D785 applies to the Rockwell Hardness figure given, and ASTM test method D22450 applies to the Shore Hardness figures given.
[1]Scientific Polymer Products Catalog 801;
[2]Average Molecular Weight;
[3]Molecular Weight Range;
[4]The Merck Index, Ninth Edition; and
[5]The polymer backbone of the ionomers consists primarily of ethylene and a vinyl co-monomer, such as methacrylic acid, thus exhibiting pendant carboxyl groups. These linear chains are "cross-linked" by ionic, inter-molecular forces through incorporation of metallic cations from Groups I or II of the periodic table. Thus, the network structure is formed by electrostatic forces similar to those in inorganic crystals rather than covalent bonds as found in typical thermosets. The cross-link density can be varied in these systems by copolymerization of various amounts of vinyl monomer with the ethylene and by varying the type and amount of metallic cations in the polymer. As with all the polymers, the physical properties are also influenced to some degree by the molecular weight distribution. Pluronic F-127 is a preferred surfactant in the cleansing composition of the invention and is an ethylene oxide-propylene oxide-propylene glycol condensation product sold by Wyandotte Chemical Corporation. The surfactant as a 20% gel by weight in purified water is optionally added to the suspension in an amount of between about 5 to 15 percent by weight of the suspension, preferably between about 8 and about 12 percent by weight.

The particulate polymer, the polyethylene glycol and Pluronic F-127, as a 20% gel in purified water, may be mixed with thimerosal, sorbic acid, EDTA, sodium chloride, and purified water to provide a sterile isotonic cleaning suspension.

To prepare a cleansing suspension polyethylene glycol having a molecular weight range form 400 to 4,000 is melted by suspending a suitable sized container, such as a beaker, containing the glycol in hot water. When the polyethylene glycol is completely melted, the beaker is removed from the heat source. The Pluronic F-127 is added with stirring until the mixture is cooled to room temperature. Upon cooling the particulate polymer is added with stirring. The optional salts and preservative are then added together with the required amount of water to provide a cleansing suspension of the desired viscosity.

For a clearer understanding of the invention, specific examples are set forth below. These examples are merely illustrative, and are not to be understood as limiting the scope and underlying principles of the invention in any way. In the following Examples the particulate polymer, which is commercially purchased, has a range of particle sizes. A certain percentage of the substance may have a particle size below 5 or even 1 micron. Hence, the particle sizes expressed in the Examples will be set forth as a range from between 0 and a size at the larger end of the range.

EXAMPLE I

A mixture of 25 grams of polyethylene glycol of a molecular weight of approximately 4000, and 30 grams of polyethylene glycol of a molecular weight of approximately 400 was melted and thoroughly mixed. With stirring 20 grams of a 20% gel in purified water of Pluronic F-127 was added to the polyethylene glycol mix. The resulting mixture was sitrred until cooled to room temperature. Upon cooling 10 grams of Natural (10/15) ES (which is a trademark of Rislan Corporation and is Nylon-11 electrostatic extrude of a particle size range between 0 to 44 microns) was added with stirring to the polyethylene glycol and Pluronic mixture. With stirring 15 ml of purified water was added to the mixture and stirring was continued until a smooth suspension was formed.

EXAMPLE II

As in Example I, 25 grams of Pluronic F-127 20% gel was added with stirring to a melted mixture of 25 grams of polyethylene glycol of a molecular weight of approximately 4000, and 30 grams of polyethylene glycol of a molecular weight of approximately 400. The resulting mixture was stirred until cooled to room temperature, whereupon 10 grams of Polymer H0050/80 (which is a trademark of Rislan Corporation and is Nylon-11 of a particle size range between 0 to 80 microns) was added with stirring to the polyethylene glycol and Pluronic mixture. With stirring 10 ml of purified water was added to the mixture and stirring was continued until a smooth suspension was formed.

EXAMPLE III

As in Example I, 35 grams of Pluronic F-127 20% gel was added with stirring to a melted mixture of 25 grams of polyethylene glycol of a molecular weight of approximately 4000, and 30 grams of polyethylene glycol of a molecular weight of approximately 400. The resulting mixture was stirred until cooled to room temperature, whereupon 10 grams of French-Naturelle ES (which is a trademark of Rislan Corporation and is Nylon-11 electrostatic extrude of a particle size range between 0 to 80 microns) was added with stirring to the polyethylene glycol and Pluronic mixture. Stirring of the mixture was continued until a smooth suspension was formed.

EXAMPLE IV

As in Example I, 35 grams of Pluronic F-127 20% gel was added with stirring to a melted mixture of 25 grams of polyethylene glycol of a molecular weight of approximately 4000, and 30 grams of polyethylene glycol of a molecular weight of approximately 400. The resulting mixture was stirred until cooled to room temperature, whereupon 10 grams of CAB 381-20 (which is a trademark of Eastman Chemical Co. and is cellulose acetate butyrate of a particle size range between 0 to 120 microns) was added to the polyethylene glycol and Pluronic mixture. Stirring of the mixture was continued until a smooth suspension was formed.

EXAMPLE V

As in Example I, 25 grams of Pluronic F-127 20% gel was added with stirring to a melted mixture of 25 grams of polyethylene glycol of a molecular weight of approximately 4000, and 30 grams of polyethylene glycol of a molecular weight of approximately 400. The resulting mixture was stirred until cooled to room temperature, whereupon 12.5 grams of Naturell Fine (which is a trademark of Rislan Corporation and is Nylon-11 of a particle size range between 0 to 45 microns) was added with stirring to the polyethylene glycol and Pluronic mixture. With constant agitation 0.02 grams of a 1.0% aqueous solution of thimerosal and 0.9 grams of sodium chloride were mixed into the glycol-Pluronic-Naturell Fine mixture to form the cleaning composition. After addition of the thimerosal and sodium chloride, with continued stirring purified water was added to bring the total weight of the composition to 100 grams and a smooth suspension was formed.

EXAMPLE VI

As in Example I, 25 grams of Pluronic F-127 20% gel was added with stirring to a melted mixture of 25 grams of polyethylene glycol of a molecular weight of approximately 4000, and 30 grams of polyethylene glycol of a molecular weight of approximately 400. The resulting mixture was stirred until cooled to room temperature, whereupon 10.0 grams of polyethylene F-N500 (which is a product of U.S. Industrial Chemicals and is low density polyethylene of a particle size of less than 20 microns) was added with stirring to the polyethylene glycol and Pluronic mixture. With constant agitation 0.02 grams of an aqueous solution of thimerosal and 0.9 grams of sodium chloride were mixed into the glycol-Pluronic- polyethylene mixture to form the cleaning composition. After the addition of the thimerosal and sodium chloride, with continuous stirring purified water was added to bring the total weight of the composition to 100 grams and a smooth suspension was formed.

EXAMPLE VII

In a beaker 0.8 grams of hydroxy ethyl cellulose having a molecular weight of approximately 15,000 and 0.5 grams Tween 21 is dispersed into about 40 ml of purified water. The mixture then is sterilized by autoclaving at 121° C. under a pressure of 18 psi for ½ hour. In another beaker 0.6 gram sodium chloride, 0.2 gram boric acid, 0.1 gram EDTA-disodium, 0.25 gram sodium borate qs to pH 7.6 and 0.4 ml of a 1.0% aqueous solution of thimerosal is dissolved and mixed with constant agitation into 40 ml of purified water. This mixture is then pressure filtered into the first mixture using a sterile millipore setup fitted with a 0.2 micron filter. The two mixtures are then homogeneously mixed.

10 grams of French Naturelle beads, sterilized at 121° C. at 18 psi for ½ hour, are added to the homogeneous mixture with constant agitation. With continuous stirring purified water was added to the latter mixture to bring the total weight of the composition to 100 grams and to form a smooth suspension.

EXAMPLE VIII

A mixture of 30 grams of polyethylene glycol of a molecular weight of approximately 4000, and 40 grams of polyethylene glycol of a molecular weight of approximately 400 was melted in a beaker by suspending the beaker into hot water. After the polyethylene glycol was completely melted, it was thoroughly mixed with a glass rod to form a smooth ointment base. The ointment base was transferred onto a porcelain tile and was mixed with a spatula with 15 grams of Natural ES (10/15) to form an ointment. With continued stirring purified water was incorporated into the ointment to bring the total weight of the composition to 100 grams and to soften and smooth the resulting cleansing ointment.

EXAMPLE IX

A mixture of 50 grams of polyethylene glycol of a molecular weight of approximately 4000, and 30 grams of polyethylene glycol of a molecular weight of 400 was melted and mixed as in Example VIII. After mixing and melting, as in Example VIII, the glycol mixture was mixed with 10 grams of Natural ES and further mixed with purified water to bring the total weight of the composition to 100 grams and to provide a soft smooth cleansing ointment.

EXAMPLE X

A mixture of 25 grams of polyethylene glycol of a molecular weight of approximately 4000, and 30 grams of polyethylene glycol of a molecular weight of 400 was melted and mixed as in Example VII. After mixing and melting, 25 grams of a 20% gel in purified water of Pluronic F-127 and 10 grams of Polymer H0050/80 were added and mixed into the polyethylene glycol to provide an ointment. With continued mixing purified water was incorporated into the ointment to bring the total weight of the composition to 100 grams and to soften and smooth the resulting cleansing ointment.

STUDY I

A study was designed to determine the non-abrasive nature of the polymeric cleaner formulation.

Five unused lenses of each of the six brands of contact lenses were selected for the non-abrasive test. The six brands of contact lenses selected were:

Polycon—Syntex
Tesicon—Uricon
TRESOFT—Alcon Laboratories, Inc.
Silicon—Wohlk
CAB—Danker Wohlk
PMMA—Standard Hard Lenses To determine the non-abrasive nature of the polymeric cleaner formulations, all the lenses were viewed through the Bausch & Lomb Optical Microscope under 40× magnification for scratches and/or cuts on lens surface. It was noted that almost all types of lenses had some surface scratches.

Each brand of lenses was then cycled through a cleaning regimen. The lens was rubbed with 2 to 3 drops of polymeric cleaner of Example VIII in the palm of the hand with the index finger for a total of 20 seconds and rinsed with normal saline. This procedure was repeated for a total of fifty cycles on each lens. The lenses were viewed for scratches after 5, 10, 20, 30, 40 and 50 cleaning cycles using the Bausch & Lomb Optical Microscope under 20× and 100× magnifications. Photographs were taken.

The lens photographs indicate no sign of new cuts and/or scratches on the lens surfaces under study.

The efficacy of polymeric cleaner was determined on laboratory deposited as well as human worn soft contact lenses.

STUDY II

In the laboratory, soft contact lenses were soiled with artificial deposition model solution, containing 0.05 percent by weight lysozyme 3× protein and 0.05% percent by weight mucin type 2 in isotonic solution to pH 7.0. The deposition of clean lenses involved heating the lenses with a 5 ml of deposition model solution in stoppered glass vial for one hour at 92° C. The above procedure was repeated two times with fresh depositions model solution to obtain heavier deposits of protein on the lens surface.

The deposited lens was then rubbed with 2 to 3 drops of the polymer cleaner of Example VIII in the palm of the hand with the index finger for a total of 20 seconds (both sides of the lens) and rinsed with normal saline. Depending on the extent of protein deposit on the lens, one to two applicatons of polymeric cleaner of Example VIII was needed to clean the protein from the lens.

STUDY III

In another efficacy study, human worn soft contact lenses having protein encrustations were collected and cleaning efficacy of the polymeric cleaner was determined following a similar cleaning regimen as described above. Six sets of human worn lenses were used for the efficacy study and all the lenses were effectively cleaned, and the protein encrustations were removed.

STUDY IV

Tresoft soft hydrophilic contact lenses which are products of Alcon Laboratories, Inc. were subjected to encrustation with a Model 1 deposition solution containing purified water, 0.05% by weight lysozyme 3× crystallized protein, 0.05% by weight porcine stomach mucin type II, and 0.09% by weight NaCl to pH 7.0, using sodium hydroxide. The lenses were subjected to encrustation by immersing them into 5 ml of the model solution in a stoppered glass vial, heating the contents to about 92° C. for one hour, and cooling the lenses. The latter procedure was repeated two times with fresh model solution to obtain heavier deposits of protein on the lens surface.

The cleaning efficacy of various polymeric powders was tested such powders including low density particulate polyethylene, particulate cellulose acetate butyrate, particulate polycarbonate and particulate Nylon 11, all of which are shown in TABLE II.

TABLE II

Low Density Polyethylene

MicrotheneMN 722*
Microthene-F FA-520*
Microthene-F FN-500*
*Products of U.S. Industrial Chemical Co.

Cellulose Acetate Butyrate

CAB-500-1**
CAB-500-5**
CAB-531-1**
**Products of Eastman Kodak Chemical Co.

Polycarbonate

Merlon 5300 U***
***Product of Mobay Chemical Corporation

Poly (11-undecamide) or Nylon 11

H005 0/80****
H005 200/300****
French Natural HV****
Natural ES 15/10****
Natural FB 15/10****
Orgasol 2002D****
French Natural ES****
****Products of Rilsan Corp.

Small amounts of each of the particulate polymers listed in TABLE II were mixed into 4 to 5 drops of saline solution. Each mixture then was used to clean a pair of the Tresoft soft contact lenses which were subjected to the two desposition cycles described above. The lenses were cleaned by rubbing them with a few drops of cleaner for about 20 seconds.

The various polymeric powders then were evaluated for their efficacy. After the deposition cycles and each cleaning, the lenses were visually examined and classified according to the Rudko scale. The results of the tests are shown in Table III below.

TABLE III

EFFICACY (RATING* OF LENSES)

| Polymer | Lens | Before Cleaning | After Cleaning 1 | 2 | 3 |
|---|---|---|---|---|---|
| Polyethylene (low density powder) | | | | | |
| Microthene MN 722 | 1 | III FD | III FA | III FA | I |
| | 2 | III FC | III FC | III FA | I |
| Microthene-F FA-520 | 1 | IV FD | II FC | II FC | I |
| | 2 | IV FD | II FB | II FC | I |
| Microthene-F FN-500 | 1 | III FD | II FA | I | — |
| | 2 | III FD | II FB | I | — |
| Cellulose Acetate Butyrate | | | | | |
| CAB-500-1 | 1 | IV FC | III FA | II FA | I |
| | 2 | IV FD | III FA | III FA | I |
| CAB 500-5 | 1 | IV FD | III FC | I | — |
| | 2 | IV FD | III FD | II FC | I |
| CAB 531-1 | 1 | III FC | II FB | I | — |
| | 2 | III FC | II FC | I | — |
| Polycarbonate | | | | | |
| Merlon 5300 U | 1 | IV FC | I | — | — |

TABLE III-continued

EFFICACY (RATING* OF LENSES)

| Polymer | Lens | Before Cleaning | After Cleaning 1 | 2 | 3 |
|---|---|---|---|---|---|
| | 2 | IV FD | I | — | — |
| Polyamide(Poly 11-undecamide or Nylon 11) | | | | | |
| H005 0/80 | 1 | III FD | II FB | I | — |
| | 2 | III FD | II FC | I | — |
| HOO5 200/300 | 1 | IV FD | II FA | I | — |
| | 2 | IV FD | II FA | I | — |
| H005 300/500 | 1 | III FD | II FA | I | — |
| | 2 | III FD | II FC | I | — |
| French Natural | 1 | IV FD | II FC | I | — |
| HV | 2 | III FD | II FC | I | — |
| Natural ES 15/10 | 1 | IV FC | I | — | — |
| | 2 | IV FC | I | — | — |
| Natural FB 15/10 | 1 | IV FC | I | — | — |
| | 2 | III FD | I | — | — |
| Orgasol 2002 D | 1 | III FD | II FC | I | — |
| | 2 | IV FC | II FA | I | — |
| French Natural | 1 | IV FD | I | — | — |
| ES | 2 | IV FC | I | — | — |

In the Table, the deposits on the lenses generally were classified according to the Rudko system. Heaviness of deposits were classified as:
I clean;
II deposits are visible under oblique light when wet using 7X magnification;
III deposits when dry are visible to unaided eye without special light; and
IV deposits when wet are visible to unaided eye.
The extent of deposits were classified as:
A 0-25% of lens surface contained deposits;
B 25-50% of lens surface contained deposits;
C 50-75% of lens surface contained deposits;
D 75-100% of lens surface contained deposits; and
E Deposits filmy as opposed to patchy or crystalline.

The invention in its boarder aspects is not limited to the specific details shown and described, but departures may be made from such details within the scope of the accompanying claims without departing from the principles of the invention and without sacrificing its advantages.

What is claimed is:

1. An aqueous ophthalmic cleansing composition for cleaning a soft contact lens comprising an effective amount of a substantially spherical particulate polymer for removal of proteinaceous and lipid deposits on said soft contact lens, said particulate polymer selected from the group consisting of polyethylene, cellulose acetate butyrate, polycarbonate, poly 11-undecamide, polyvinyl chloride and mixtures thereof wherein said particulate polymers have a particle size in the range from about twenty microns to about one hundred microns, a carrier in which said particulate polymer is suspended, said carrier having a viscosity sufficient to keep the particulate polymer in suspension and a preservative, to provide an isotonic cleansing composition.

2. A cleansing composition as recited in claim 1 wherein said particulate polymer is precipitated from solution, said precipation rendering the shape of said particles of said polymer.

3. A cleansing composition as recited in claim 2 wherein said carrier is compatible with ocular tissue and comprises a thickener wherein said thickener is selected from the group consisting of polyethylene glycol, carboxy vinyl polymers, cellulose, hydroxyethyl cellulose, methoxy cellulose, low molecular weight hydroxylethylmethacrylate, polyvinyl alcohol, polyvinylpyrrolidine and mixtures thereof.

4. A cleansing composition as recited in claim 2 wherein said particulate polymer is poly 11-undecamide.

5. A cleansing composition as recited in claim 2 wherein said composition includes sodium chloride.

6. A cleansing composition as recited in claim 5 wherein said particulate polymer is poly 11-undecamide.

7. An aqueous ophthalmic cleansing composition for cleaning a soft contact lens as recited in claim 1 wherein said particulate polymer is poly 11-undecamide.

8. A cleansing composition as recited in claim 1, wherein said particulate polymer comprises from about 5 to about 20 percent by weight of said composition.

9. A cleansing composition as recited in claim 8 wherein said particulate polymer is poly 11-undecamide.

10. An aqueous ophthalmic cleansing composition for cleaning a contact lens comprising an effective amount of a substantially spherical particulate polymer for the removal of proteinaceous and lipid deposits on said contact lens, said particulate polymer selected from the group consisting of polyethylene, cellulose acetate butyrate, polycarbonate, poly 11-undecamide, polyvinyl chloride and mixtures thereof wherein said particulate polymer has a particle size from about twenty microns to about one hundred microns, and a carrier in which said particulate polymer is suspended, said carrier having a viscosity sufficient to keep the particulate polymer in suspension and a preservative, to provide an isotonic cleansing composition.

11. A cleansing composition as recited in claim 10 wherein said carrier is compatible with ocular tissue and comprises a thickener wherein said thickener is selected from the group consisting of polyethylene glycol, carboxy vinyl polymers, cellulose, hydroxyethyl cellulose, methoxy cellulose, low molecular weight hydroxyethylmethacrylate, polyvinyl alcohol, polyvinylpyrrolidine and mixtures thereof.

12. A cleansing composition as recited in claim 11 wherein said particulate polymer is precipitated from solution, said precipitation rendering the shape of said particles of said polymer.

13. A cleansing composition as recited in claim 11 wherein said particulate polymer is poly 11-undecamide.

14. A cleansing composition as recited in claim 3 wherein said particulate polymer is precipitated from solution, said precipitation rendering the shape of said particles of said polymer.

15. A cleansing composition as recited in claim 14 wherein said composition includes sodium choride.

16. A cleansing composition as recited in claim 10 wherein said particulate polymer comprises from about 5 to about 20 percent by weight of said composition.

17. A cleansing composition as recited in claim 10 wherein said particulate polymer is poly 11- undecamide.

18. A cleansing composition as recited in claim 17 wherein said poly 11-undecamide comprises from about 5 to about 20 percent by weight of said composition.

19. A cleansing composition as recited in claim 10 wherein said composition includes sodium chloride.

* * * * *

UNITED STATES PATENT AND TRADEMARK OFFICE

CERTIFICATE OF CORRECTION

PATENT NO. : 4,493,783
Page 1 of 2
DATED : JANUARY 15, 1985

INVENTOR(S) : KAI C. SU ET AL.

It is certified that error appears in the above-identified patent and that said Letters Patent is hereby corrected as shown below:

IN THE SPECIFICATION

Column 3, line 14, delete "be" second occurrence; and
line 14, change "cleaning" to --cleansing--.
Column 5-6, line 17, change "$100,00^4$" to --$100,000^4$--.
Column 5, line 45, change "cleaning" to --cleansing--;
line 47, change "form" to --from--; and
line 53, after "cooling" insert --,-- (comma).
Column 6, line 48, change "sitrred" to --stirred--;
line 50, change "Rislan" to --Rilsan--; and
line 66, change "Rislan" to --Rilsan--.
Column 7, line 12, change "Naturelle" to --Natural--;
line 13, change "Rislan" to --Rilsan--;
line 40, change "Naturell" to --Natural--;
line 41, change "Rislan" to --Rilsan--; and
line 46, change "Naturell" to --Natural--.
Column 8, line 20, change "Naturelle" to --Natural--.
Column 9, line 35, delete "%" (percent sign); and
line 48, change "applicatons" to --applications--.
Column 10, line 7, after "tested" insert --,-- (comma); and
line 42, change "desposition" to --deposition--.

UNITED STATES PATENT AND TRADEMARK OFFICE
CERTIFICATE OF CORRECTION

PATENT NO. : 4,493,783

DATED : JANUARY 15, 1985

INVENTOR(S) : KAI C. SU ET AL.

It is certified that error appears in the above-identified patent and that said Letters Patent is hereby corrected as shown below:

IN THE CLAIMS

Claim 2, column 11, line 55, change "precipation" to --precipitation--.

Claim 3, column 11, line 63-64, change "hydroxylethylmeth-acrylate" to --hydroxyethylmethacrylate--.

Claim 14, column 12, line 47, change "3" to --10--.

Signed and Sealed this

Eighth Day of September, 1987

*Attest:*

DONALD J. QUIGG

*Attesting Officer* *Commissioner of Patents and Trademarks*